United States Patent
Kornas (10) Patent No.: US 9,596,892 B1
(45) Date of Patent: Mar. 21, 2017

(54) METHOD AND APPARATUS FOR TEXTURED BRA INSERT

(71) Applicant: Angela T. Kornas, Hatfield, PA (US)

(72) Inventor: Angela T. Kornas, Hatfield, PA (US)

(73) Assignee: honey cloudz LLC, Hatfield, PA (US)

( * ) Notice: Subject to any disclaimer, the term of this patent is extended or adjusted under 35 U.S.C. 154(b) by 0 days.

(21) Appl. No.: 15/224,536

(22) Filed: Jul. 30, 2016

Related U.S. Application Data (60) Provisional application No. 62/299,926, filed on Feb. 25, 2016.

(51) Int. Cl.
*A41C 3/14* (2006.01)
*A61F 2/52* (2006.01)
*A41C 3/08* (2006.01)
*A41C 3/00* (2006.01)
*A41C 3/04* (2006.01)

(52) U.S. Cl.
CPC ........... *A41C 3/144* (2013.01); *A41C 3/0092* (2013.01); *A41C 3/04* (2013.01); *A41C 3/08* (2013.01); *A61F 2/52* (2013.01)

(58) Field of Classification Search
CPC ....... A41C 3/00; A41C 3/0028; A41C 3/0085; A41C 3/146; A41C 3/144; A41C 3/065; A41C 3/14; A41C 3/10; A41C 3/007; A41C 3/0014; A41C 3/105; A41D 13/0153
USPC .............. 450/37–39, 54–57, 81; 2/267, 268; 623/7, 8
See application file for complete search history.

(56) References Cited

U.S. PATENT DOCUMENTS

| | | | | |
|---|---|---|---|---|
| 5,584,883 A | * | 12/1996 | Wild | B29C 43/18 623/7 |
| 5,755,611 A | * | 5/1998 | Noble | A41C 3/065 450/39 |
| 6,015,332 A | | 1/2000 | Lee | |
| 6,419,548 B1 | * | 7/2002 | Wittes | A41C 3/065 2/267 |
| 6,519,781 B1 | * | 2/2003 | Berns | A41D 13/0153 2/267 |
| 6,857,932 B2 | * | 2/2005 | Chen | A41C 3/146 2/267 |
| 7,959,488 B2 | | 6/2011 | Talamo | |
| 8,118,639 B1 | * | 2/2012 | Boon | A41C 3/144 450/37 |
| 8,827,765 B2 | | 9/2014 | Zhang | |
| 2005/0003736 A1 | * | 1/2005 | Bentham | A41C 3/0014 450/75 |
| 2005/0164602 A1 | | 7/2005 | Armstrong | |
| 2005/0266770 A1 | * | 12/2005 | Henricksen | A41C 3/0007 450/1 |
| 2008/0194180 A1 | * | 8/2008 | Warren | A41C 3/10 450/57 |
| 2011/0143633 A1 | * | 6/2011 | Zhang | A41C 3/14 450/39 |

(Continued)

OTHER PUBLICATIONS http://thelingerie.uk/shop/the-original-bra-crumpets-uniquely-perforated-silicone-adhesive-bikinibraswimwear-booster-pads/.

*Primary Examiner* — Gloria Hale
(74) *Attorney, Agent, or Firm* — San Diego Patent Prep & Pros, Inc.; Mary Fales (57) ABSTRACT

The disclosed embodiments are for a method and apparatus for textured bra insert/s. The insert may be constructed with an outer layer (or outer side) that faces the garment. The texture may comprise a raised pattern of geometrical shapes of silicone or equivalent functioning material.

20 Claims, 6 Drawing Sheets

(56) References Cited

U.S. PATENT DOCUMENTS

| | | | |
|---|---|---|---|
| 2012/0208434 A1* | 8/2012 | Chang | A41C 3/0085 450/81 |
| 2012/0231700 A1* | 9/2012 | Chou | A41C 3/0028 450/39 |
| 2015/0257456 A1* | 9/2015 | Turlan | A41C 3/105 450/39 |

* cited by examiner

METHOD AND APPARATUS FOR TEXTURED BRA INSERT

CLAIM TO PRIORITY UNDER 35 U.S.C. §119

The present Application for Patent claims the benefit of U.S. Provisional Application No. 62/299,926 filed on Feb. 25, 2016, entitled, "Textured Bra Inserts," of which is expressly incorporated herein by reference in its entirety.

BACKGROUND

I. Field

The disclosed embodiments relate to garment insert/s and more specifically to bra inserts that are textured.

II. Background

People today want to augment, shape, or enhance their breast appearance for a variety of reasons and applications. Plastic surgery can be costly and some people may not want the medical risks associated with surgery. Others experiencing a mastectomy may need to wait for reconstruction, or don't want breast reconstruction. Moreover, built in inserts, some removable inserts, or solid silicone type inserts have problems. For example, they may not stay in place, be heavy, awkward feeling, or cause unpleasant perspiration. Common removable type or solid silicone inserts may shift about causing the appearance of unnatural or mismatched shaped breasts. Also, the color of the insert may be visible next to skin. All of which may be an embarrassing situation for the user. Most built in pads are built in and can not be customized or removed to accommodate the changes each individual may desire. For example, a person may buy a swim suit top that comes with built in padding. They may desire to have more padding than the built in, or change the breast shape, but the inserts that come built into the swim suit top are static. Also, if they desire to use a removable insert as available today, it may not stay in place, may not be the shape, size, color, weight, or look the woman desires. In addition, the inserts are often aesthetically unattractive. Moreover, a person who invests in specialty inserts will want to be able to reuse them with as many garments as they desire. Furthermore, another problem with available removable inserts is the fact that they bunch up when washed, and/or loose their ability to keep shape after being washed. Therefore, there is a need in the art for a textured, light weight, low perspiration, removably secure, variable use, aesthetically pleasing, and form keeping bra insert/s that stay in place while in use in a variety of applications.

SUMMARY

Disclosed are embodiments for a method and apparatus for textured bra insert/s. In an embodiment, a textured bra insert is disclosed, comprising: an outer layer comprising textured fabric, the textured fabric comprising stretchable fabric deposited with a raised pattern of discontinuous geometric shaped raised pattern material; an inner layer comprising fabric; a padding layer positioned in-between the inner and outer layers; and the outer layer, padding layer, and inner layer are joined together.

In another embodiment, a textured bra insert is disclosed, comprising: an outer layer comprising textured fabric, the textured fabric comprising stretchable fabric deposited with a raised pattern of discontinuous hexagon shaped silicone material; an inner layer comprising moisture wicking fabric; a padding layer positioned in-between the inner and outer layers; and the outer, padding, and inner layers are joined together.

In yet another embodiment, a textured bra insert is disclosed, comprising: a 3-D spacer pad, comprising an outside surface and an inside surface; the 3-D spacer pad outside surface having been deposited before molding with a raised pattern of discontinuous geometric shaped raised pattern material; and the 3-D spacer pad molded into a cup shape after the raised pattern of discontinuous geometric shaped raised pattern material is deposited.

BRIEF DESCRIPTION OF THE DRAWINGS

The following embodiments may be better understood by referring to the following figures. The figures are presented for illustration purposes only, and may not be drawn to scale or show every feature, orientation, or detail of the embodiments. They are simplified to help one of skill in the art understand the embodiments readily, and should not be considered limiting.

DETAILED DESCRIPTION

Each of the additional features and teachings disclosed below can be utilized separately or in conjunction with other features and teachings to provide a method and apparatus for textured garment inserts. The raised textured fabric used as well as a method of making the raised textured fabric is also disclosed. Representative examples of the following embodiments, will now be described in further detail with reference to the attached drawings. This detailed description is merely intended to teach a person of skill in the art details for practicing the preferred aspects of the teachings and is not intended to limit the scope of the embodiments.

The disclosed embodiments describe a method and apparatus for textured bra insert/s. The insert/s may be used with any garment of choice. For example, garments including, but not limited to, dresses, shirts, bras, strapless garments, evening wear, swimsuits, swimwear, lingerie, or sportswear. In an embodiment, the textured inset/s may be a shoulder pad. In another embodiment, the insert/s may be nursing pad insert/s. The disclosed insert/s embodiments describe an insert whose construction allows for the insert/s to be washed and not bunch and/or retain its form after washing.

The disclosed inserts can be a variety of shapes and colors for desired effects. In some embodiments, the insert/s may be generally convex shaped as is well known in the industry as a demi, full, push-up, or mini-push-up. In an embodiment, the shape of the insert/s may be customized to work with a specific garment. For example, the shape of popular swim suit top. In another embodiment, the insert/s may be of such a size and shape as to be a fake "breast." For example, a woman may have had one breast surgically removed, and require the need for a textured insert that is fuller and shaped more like a full breast. This embodiment may be an attractive alternative to traditional breast prosthetics. Moreover, in yet another embodiment, the left and right insert/s of a pair may be of different sizes and/or shapes to help even out misshaped breasts, because some women are born with unequally shaped/sized breasts.

The textured insert/s provide an adhering function while in use by way of depositing a gripping raised pattern onto fabric (or the outer surface of an insert). The disclosed insert/s may be textured on the outer side of the insert. The outer side of the insert is the side that contacts garments. The inner side of the insert is the side that contacts skin (or is towards the body). A textured effect on the outside of the insert/s may allow for the insert/s to temporarily adhere to garments: such that the insert/s stays in place where positioned. If the insert/s stick to the users skin, then there may be less control over the overall look of the outfit. The texture may be created by adhering a flexible (elastic) but semi-tacky material in a raised pattern on the fabric. The raised pattern may be a specifically designed pattern suitable for the fabric it is being applied to in the form of raised spaced apart geometric shapes deposited on the outer side or outer fabric of the insert/s. The embodiments herein primarily are described in examples of the textured insert/s, but the fabric itself with the texture on it is also a disclosed embodiment. In order for the application to be concise, it is to be understood to a person of ordinary skill in the art, that discussion of the texture embodiments through this application is equally true for the outer fabric embodiments as well as for the insert/s that use the fabric. The material (raised pattern material) used to create the raised pattern may be a variety of materials such as silicone or equivalent functioning material. In an embodiment, the material used to deposit onto the outer side fabric or outer layer of the insert/s to create the textured raised pattern has a Shore A factor between 30-80 Shore A.

Figure 1A:
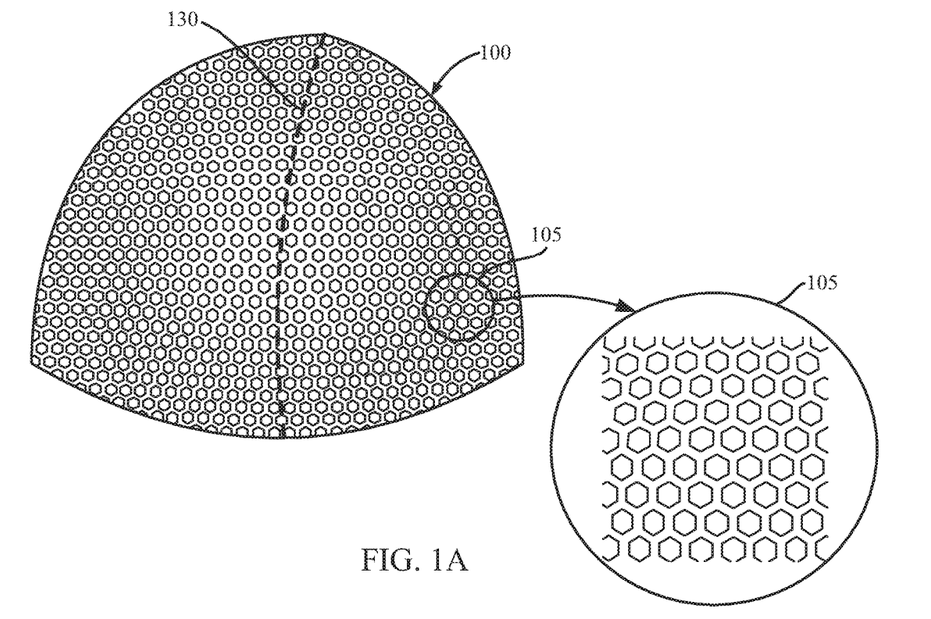
FIG. 1A. illustrates a front view of a textured insert/s in an embodiment(s).
Figure 1B:
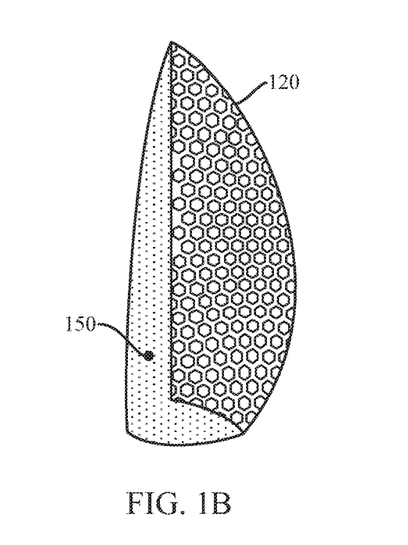
FIG. 1B. illustrates a side view of a textured insert/s in an embodiment(s).
Figure 2A:
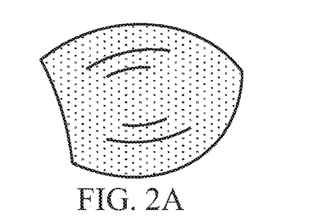
FIG. 2A. illustrates a Bandeau shaped textured insert/s in an embodiment(s).
Figure 2B:
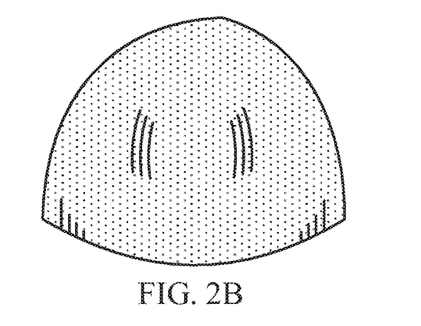
FIG. 2B. illustrates a full coverage shaped textured insert/s in an embodiment(s).
Figure 2C:
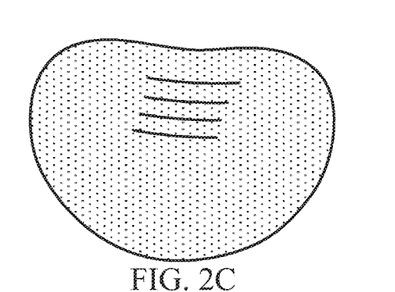
FIG. 2C. illustrates a type of mini shaped textured insert/s in an embodiment(s).
Figure 2D:
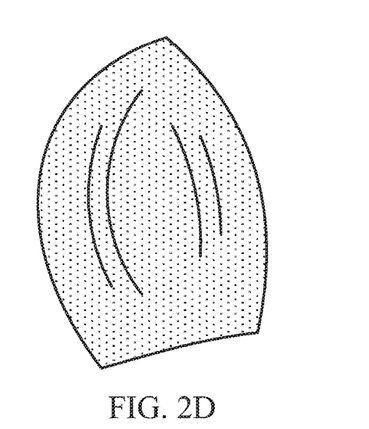
FIG. 2D. illustrates an oval shaped textured insert/s in an embodiment(s).
Figure 2E:
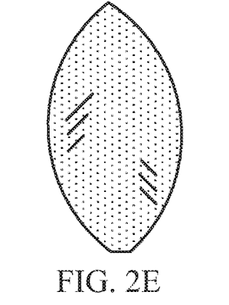
FIG. 2E. illustrates another type of mini shaped textured insert/s in an embodiment(s).
Figure 2F:
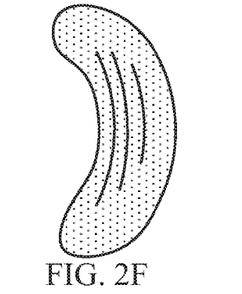
FIG. 2F. illustrates yet another type of mini shaped textured insert/s in an embodiment(s).
Figure 2G:
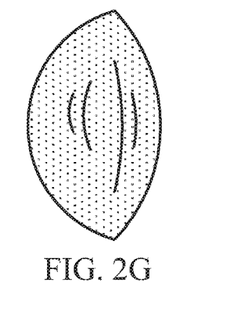
FIG. 2G. illustrates another type of mini shaped textured insert/s in an embodiment(s).
Figure 2H:
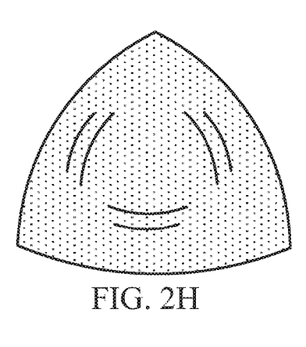
FIG. 2H. illustrates a triangle shaped textured insert/s in an embodiment(s).
Figure 2I:
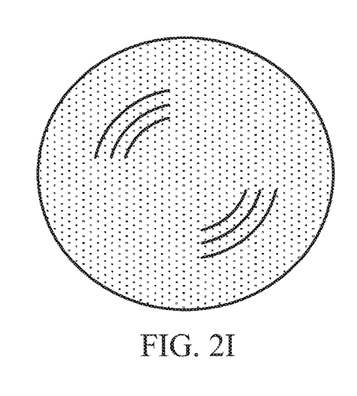
FIG. 2I. illustrates a round shaped textured insert/s in an embodiment(s).

FIG. 1A illustrates a front view of a textured insert 100 in an embodiment(s). Textured insert/s 100 in this example is shown as a full coverage shaped insert. The outer side of the insert/s 100 may be textured 105. In an embodiment, silicone or equivalent material may be adhered to fabric in a raised pattern to create the texture non-slip function. The raised pattern material may be silicone or an equivalent functioning material. In an embodiment, the insert 100 may be textured 105 with a raised pattern of hexagon shaped silicone "polka dots" 110. FIG. 1B illustrates a side view of textured insert/s 100 in an embodiment(s). The outer side 120 of the insert is shown textured in a hexagon raised pattern, but a variety of different raised patterns may be used as long as the pattern is suitable for the fabric as explained in more detail below. The inner side 150 of insert/s 100 is shown. The inner side may utilize a moisture wicking fabric to help reduce perspiration. The inner side fabric may be a 3-D spacer fabric. In an embodiment, the inner side of the insert may use a polyester and spandex, or nylon and spandex blended fabric, or other suitable fabric.

The textured insert/s 100 may be constructed in a variety of manners. In an embodiment, the insert comprises textured fabric adhered to it on a seamless cup. In another embodiment, insert/s 100 comprises a seamed cup 130. Thus, seam 130 shown in FIG. 1A is shown as optional to illustrate the two different types of general cup constructions with one figure instead of with two. A seamless cup (no seam 130) may be more desirable for applications where there may be a possibility of the seam showing through to the garment. As one of ordinary skill in the art will readily recognize, more than these two basic cup constructions are possible and are envisioned to be within the scope of the disclosed embodiments.

The insert/s can come in a variety of shapes. FIG. 2A-2I illustrates some shapes that the textured insert/s may be as is well known in the industry.

Figure 3:
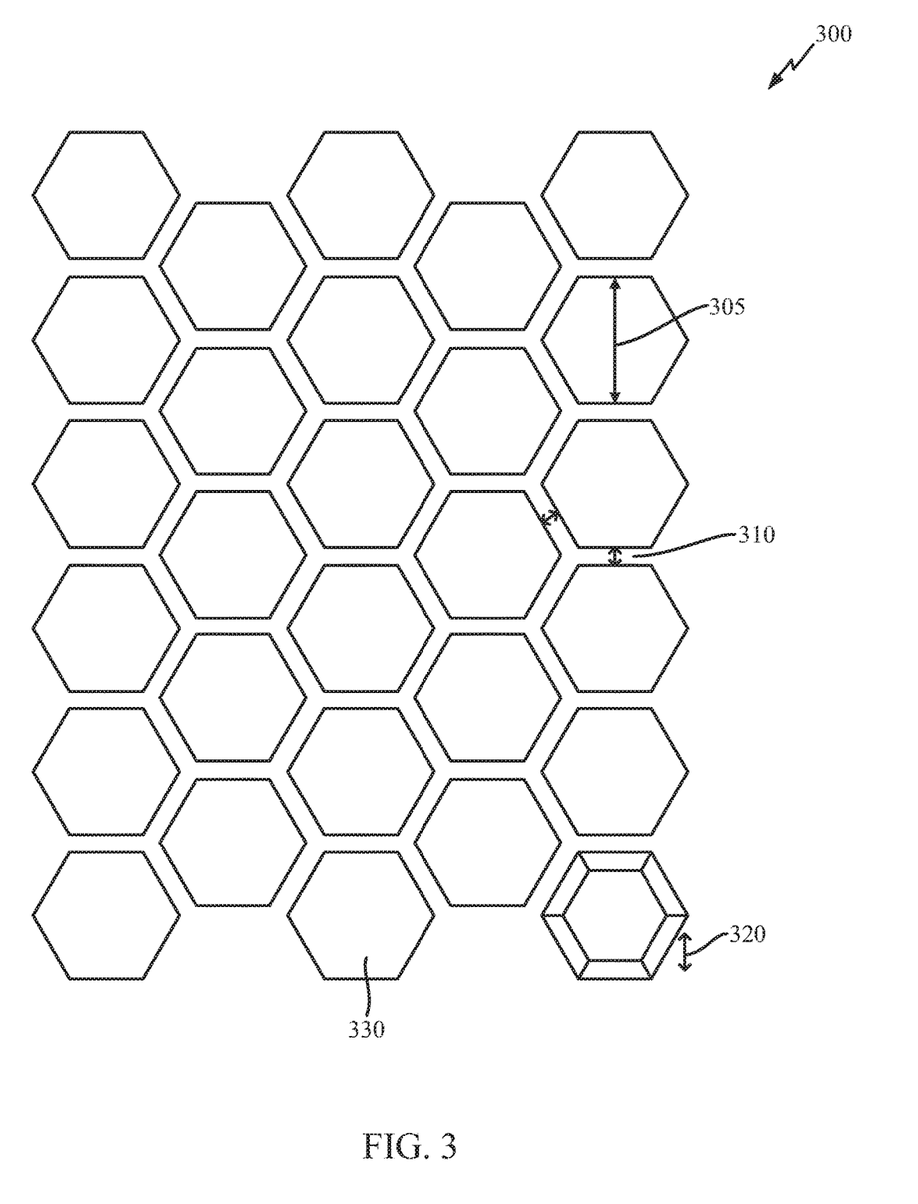
FIG. 3. illustrates a textured raised pattern in an embodiment(s).

FIG. 3 illustrates a textured raised pattern 300 in an embodiment(s). As described earlier, the "polka dots" (discontinuous raised pattern) may comprise a variety of geometric shapes 330. FIG. 3 shows hexagon "polka dot" shapes 330 as an example. In an embodiment, the "polka dot" shapes 330 may be formed using evenly spaced apart hexagon shapes. In another embodiment, the raised pattern 330 (texture) may be formed by using evenly spaced circular, oval, triangle, square, rectangle, oblong, pentagon, octagon, or other common geometric shapes. Geometric shapes with more surface area may create more strength and structural support to the outer fabric as well as gripping function to the garment. In an embodiment, the textured pattern 330 may be a series of evenly spaced lines, zigzags, circles, swirls, or other repeating geometric shapes. A discontinuous hexagon shape pattern, or specifically configured geometric design, may provide additional structural support for outer layer fabrics that are structurally weak. For example, an elastic fabric such as spandex (Lycra®) blends, do not usually have much structural support. They stretch and shift out of shape readily in multiple directions. So for example, circular dots may be used as a raised pattern in some stretchable fabrics for the outer fabric when the outer side fabric has more structure. However, for fabrics like spandex blends, then the hexagon raised pattern (or structurally similar) shape may be better. In an embodiment, the raised shapes are beveled (or tapered) on their edges such that there may be no distinct shape start and stop edges. In an embodiment, the shapes are positioned to minimize lines showing through from the insert to the garment. For example, shapes placed close together may give a smoother effect than shapes spaced too far apart or spaced too far apart on a section of the cup.

In an embodiment, the textured pattern 300 applied to the outer fabric (or outer insert/s surface) may be 32 geometric shapes per square inch. In another embodiment, it may be between 16-32 per square inch. In another embodiment, about 20 millimeters of discontinuous raised pattern material may be used per square inch.

In an embodiment, the size of the "raised pattern" ("polka dot") geometric shape 330 applied may be 0.125 inches (3.175 mm) in diameter 305 and 0.1875 inches in height 320

(4.763 mm). In another embodiment, the size of the geometric shape 330 applied may be between 0.063 inches (1.589 mm) and 0.5 inches (12.7 mm) in diameter 305. In another embodiment, the "raised pattern" geometric shape 330 may be between 0.063 inches (1.589 mm) and 0.375 inches (9.525 mm) in height 320 with or without tapered edges. More raised pattern material per square inch of fabric may increase the non-slipping function of the raised pattern. In contrast, applying too much material per square inch may reduce the textured fabric's ability to mold to the cup form. It may also add undesirable weight to the insert/s. Average solid silicone inserts weight around 3.5 ounces each. In contrast the average weight of the disclosed textured insert/s weigh between 0.4-1 ounce. In addition, covering the entire outer fabric with a solid sheet of silicone (or equivalent) material may shorten the life of the inserts or cause cracking in the silicone sheet. A solid sheet of non-slipping material may not conform to the cup shape as well. Moreover, a solid sheet of silicone may be less aesthetically appealing than insert/s with texture. In an embodiment, the geometric raised pattern shapes may be evenly spaced 310 apart at 0.125 inches (3.175 mm) from each other. In yet another embodiment, the geometric raised pattern shapes may be spaced 310 apart between 0.125 inches (3.175 mm) to 0.375 inches (9.525 mm) apart from each other. The geometric raised pattern shapes may be spaced evenly and symmetrically from each other or not.

In an embodiment, medical grade silicone may be used as the texture material for the raised pattern. In another embodiment, silicone alternative ET-315 may be used. Material used may have a Shore rating of between 30-80 Shore A. The silicone or equivalent material may enable the insert/s to temporality adhere to garments even if the garments get wet like a swim suit, or if the "polka dots" come into contact with an oily substance like lotion.

Figure 4:
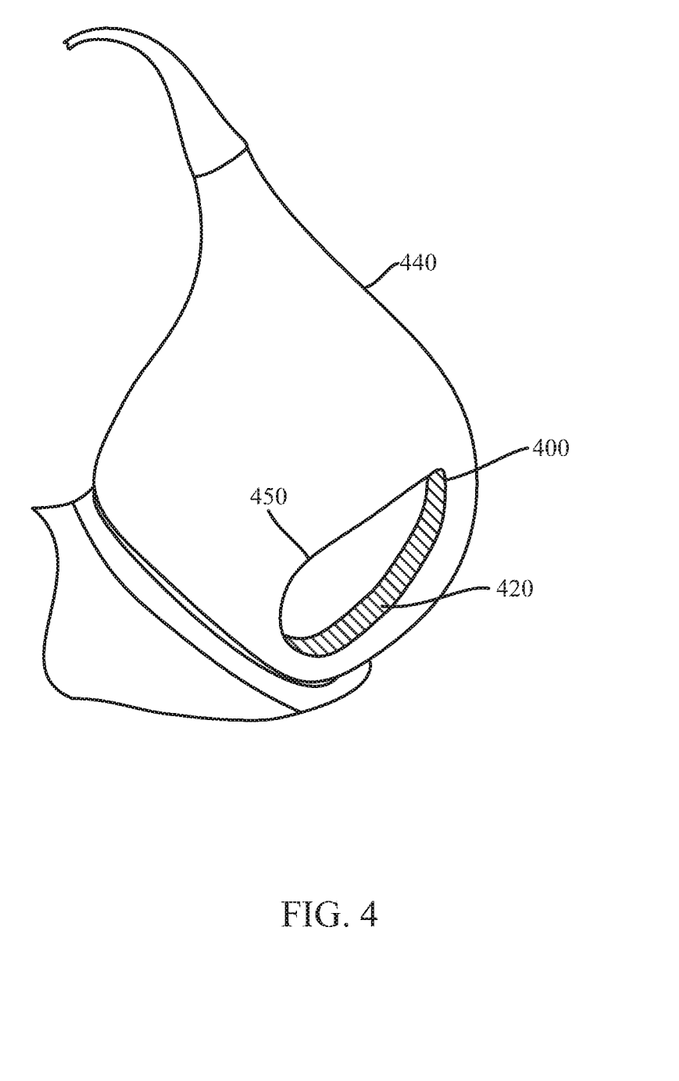
FIG. 4. illustrates a bra application of the textured insert/s in an embodiment(s).

FIG. 4. illustrates a bra application of the textured insert/s in an embodiment(s). Bra 440 is shown as a side view with the cut away details of the insert/s 400 shown. Insert/s 400 has the inner fabric 450 facing the user's skin and the outer textured fabric 420 facing the bra 440 (garment).

Figure 5:
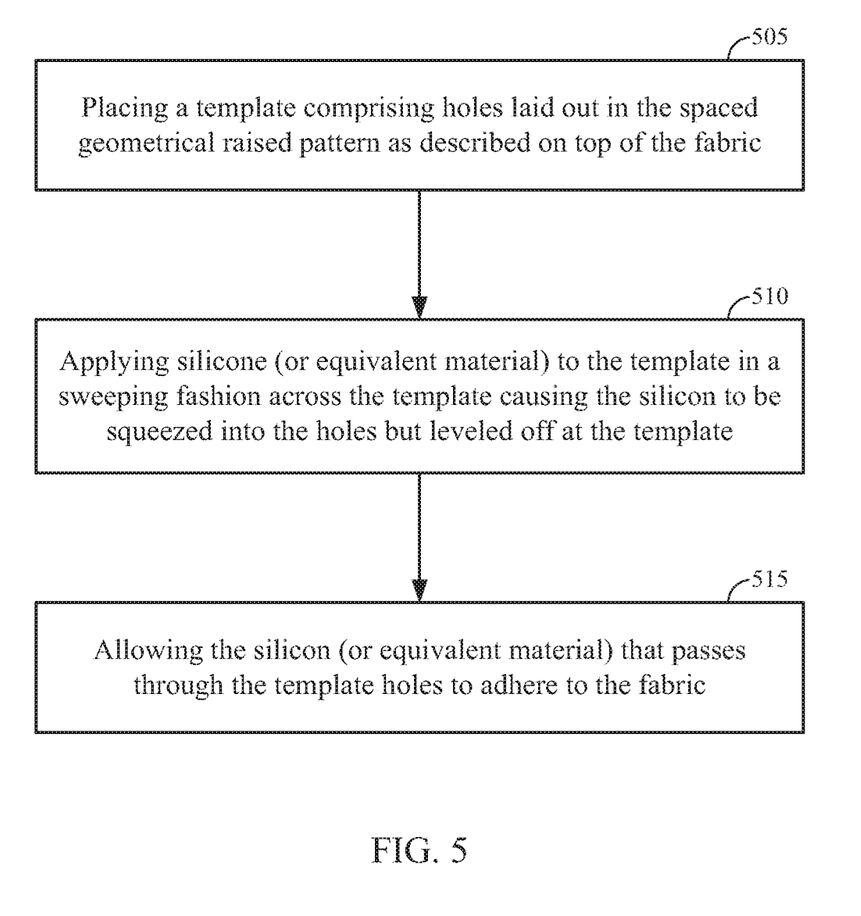
FIG. 5. illustrates a method of manufacturing the textured fabric of the embodiment(s).

FIG. 5. illustrates a method of manufacturing the textured fabric of the embodiment(s). In an embodiment, the raised pattern may be screen printed onto the outer fabric. The printing may be done with a rotary or flat bed screen printing. In step 505, a template (screen) comprising holes laid out in the spaced geometrical raised pattern as described may be placed on top of the fabric. Next at step 510, silicone (or equivalent material) may be applied to the template in a sweeping fashion across the template causing the silicon to be squeezed into the holes but leveled off at the template. The silicon or equivalent material may be heated or treated in order that the material be malleable to spread. At step 515, the silicon (or equivalent) that passes through the template holes adheres to the fabric. Finally, the fabric may be allowed to set before use. In an embodiment, the template holes used to make the raised pattern comprises evenly spaced apart hexagon shapes that may be 0.125 inches (3.175 mm) in diameter 305 and 0.1875 inches in height 320 (4.763 mm), and spaced 0.125 inches (3.175 mm) apart from each other. In an embodiment, the outer fabric used may be a spandex blend with a percentage of at least 20% spandex. The raised pattern material may be medical grade silicone with a Shore A factor between factor between 30-80 Shore A.

Figure 6A:
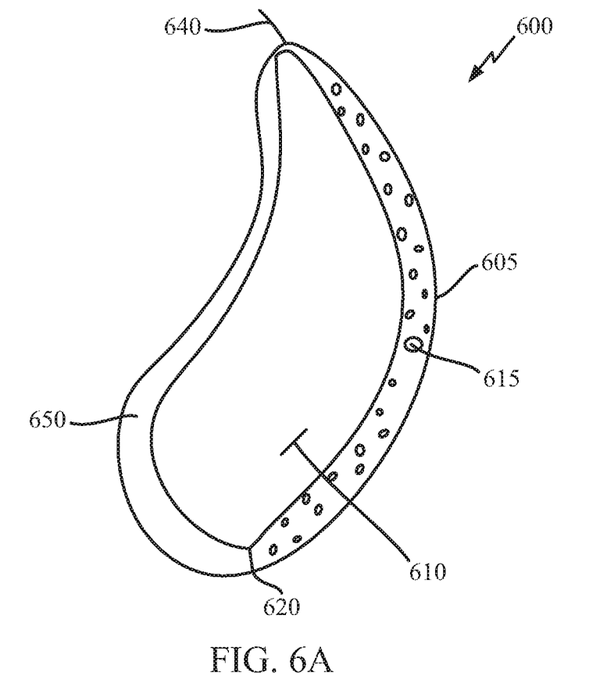
FIG. 6A. illustrates a cross sectional side view of the layers in an insert/s embodiment(s).

FIG. 6A. illustrates a cross sectional side view 600 of the layers in an insert/s embodiment(s). In this example, the insert/s may be constructed of three layers. The outer layer 605 may be textured fabric: suitable fabric with a corresponding appropriate raised "polka dot" "silicone" pattern adhered to it. The inner layer may be a padding layer 610. In this example, the shape of the cup may be shown as a demi shape, but as discussed above a variety of shapes may be accomplished. The inner layer 650 may be a moisture wicking fabric or other suitable fabric. In an embodiment, the layers are stitched together. In another embodiment, the layers are bonded as a free seam such as with ultrasonic welding (bonding) or equivalent free seam process. For example, hot air, or laser. A seam where all three layers are attached together is crudely illustrated as seam 640. However, the seam may be created by connecting only the inner 650 and out layer 605 together as crudely illustrated with seam 620 (padding layer not sewn/welded into the seam 620 with the outer and inner layers, but floats inside the outer and inner layer). In an embodiment, the padding layer comprises polyurethane.

Figure 6B:
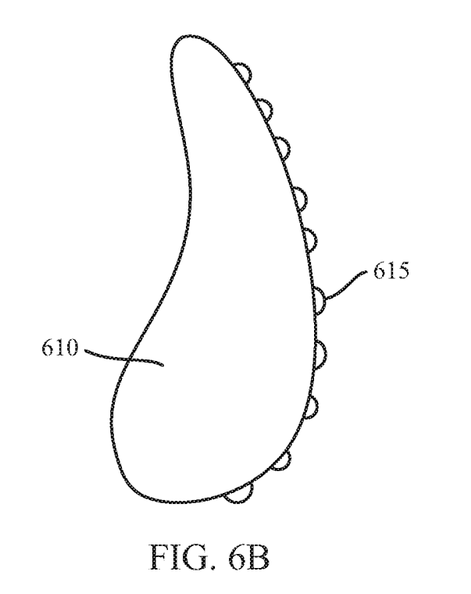
FIG. 6B. illustrates another cross sectional side view of the layers in an insert/s embodiment(s).

FIG. 6B. illustrates another cross sectional side view of the layers in an insert/s embodiment(s). The padding layer 610 comprises 3-D spacer fabric. The raised pattern of geometric shapes may be directly placed onto the 3-D spacer fabric. In this embodiment, the inner or outer layers are the 3-D spacer fabric. Then the textured 3-D spacer fabric may be molded into a cup shape.

In another embodiment, the padding layer may be a 3-D foam or 3-D spacer fabric layer that the inner and outer layers can be adhered to. In yet another embodiment, the inner padding layer comprises recycled polyurethane foam. In another embodiment, the cup may be made from a single foam mold with the raised pattern applied to the outer side of it. In an embodiment, the outer fabric the raised pattern may be applied to comprise at least 20% spandex or similar elastic material. This may help with the integrity of the "raised pattern" on the fabric. In an embodiment, inserts comprise the material polyester and spandex blend for the outer fabric that the raised pattern adheres to. In another embodiment, 3-D spacer fabric (or equivalent) comprises the outer fabric that the raised pattern adheres to. In an embodiment, inserts comprise the material nylon and spandex blend for the outer fabric that the raised pattern adheres to.

In an embodiment, the inner layer may be a trade dress or trademark color, the outer fabric (or outer layer) may be a skin tone color, and the "silicone" texture applied to the outer layer may be the same skin tone color as the outer layer (tone on tone). Skin colors include all skin tones from pale to dark to accommodate all the different skin colors. In another embodiment, the outer fabric color may be a different color than the textured pattern. For example, the outer fabric may be colored blue while the raised texture may be orange (single or multi colored "polka dots"). In an embodiment, the texture color may be clear or semi-transparent. In another embodiment, some of the raised pattern "polka dots" may be different in color from the rest of the "polka dots" in order to create another layer of aesthetics. For example, most of the "polka dots" may be colored tan while some may be colored blue to form a blue shaped image on the insert.

After reading this description, it will become apparent to a person skilled in the relevant art(s) how to implement the embodiments using other textiles as is known in the industry. The foregoing description of the preferred embodiments has been presented for purposes of illustration and description. It is not intended to be exhaustive or to limit the embodiments to the precise form or to exemplary embodiments disclosed. Obviously, many modifications and variations will be apparent to practitioners skilled in this art. Similarly, any process steps described might be interchangeable with other steps in order to achieve the same result. The embodiments were chosen and described in order to best explain the principles of the embodiments and its best mode practical application, thereby to enable others skilled in the art to understand the various embodiments and with various modifications as are suited to the particular use or implementation contemplated. It is intended that the scope of the embodiments be defined by the claims appended hereto and their equivalents. Reference to an element in the singular is not intended to mean "one and only one" unless explicitly so stated, but rather means "one or more." Moreover, no element, component, nor method step in the described disclosure is intended to be dedicated to the public regardless of whether the element, component, or method step is explicitly recited in the following claims. No claim element herein is to be construed under the provisions of 35 U.S.C. Sec. 112, sixth paragraph, unless the element is expressly recited using the phrase "means for . . . ."

In addition, the conjunction "and" when used in the claims is meant to be interpreted as follows: "X, Y and Z" means it can be either X, Y or Z individually, or it can be both X and Y together, both X and Z together, both Y and Z together, or all of X, Y, and Z together.

It should be understood that the figures illustrated in the attachments, which highlight the functionality and advantages of the described embodiments, are presented for example purposes only. The architecture of the described embodiments are sufficiently flexible and configurable, such that it may be utilized (and navigated) in ways other than that shown in the accompanying figures.

Furthermore, the purpose of the foregoing Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the described embodiments in any way. It is also to be understood that the steps and processes recited in the claims need not be performed in the order presented.

Also, it is noted that the embodiments may be described as a process that is depicted as a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function. A process or method may be implemented with a processor, or similar device, or any combination of hardware and software.

What is claimed is:

1. A textured bra insert, comprising:
   an outer layer of textured fabric, the textured fabric being stretchable and deposited with a raised pattern of discontinuous geometric shaped raised pattern material;
   an inner layer of fabric;
   a padding layer positioned in-between the inner and outer layers; and
   the outer layer, padding layer, and inner layer being joined together.

2. The textured bra insert of claim 1, wherein the geometric shape is a hexagon, circle, oval, triangle, square, rectangle, oblong, pentagon, or octagon.

3. The textured bra insert of claim 2, wherein the geometric shape is sized between 0.063 inches and 0.5 inches in diameter and is between 0.063 inches and 0.375 inches in height, and is spaced apart between 0.125 inches to 0.375 inches from each other.

4. The textured bra insert of claim 1, wherein the discontinuous geometric shapes are formed as a series of lines, zigzags, circles, swirls, or other repeating geometric shapes.

5. The textured bra insert of claim 1, wherein the inner layer includes a moisture wicking fabric in a first color;
   the textured fabric includes at least 20% spandex in a second color; and
   the raised pattern material is a medical grade silicone in a third color.

6. The textured bra insert of claim 5, wherein the second and third colors are colors selected from the set of natural skin tone colors.

7. The textured bra insert of claim 1, wherein the shape of the insert is one of a full, demi, mini, push-up, Bandeau styled, oval, round, triangle, or prosthetic breast.

8. The textured bra insert of claim 1, wherein the construction of the insert is a seamed or seamless cup.

9. The textured bra insert of claim 1, wherein the outer layer, padding layer, and inner layer are joined together seamlessly by ultra sonic welding.

10. A textured bra insert, comprising:
    an outer layer of textured fabric, the textured fabric being stretchable and deposited with a raised pattern of discontinuous hexagon shapes formed of silicone material;
    an inner layer made of moisture wicking fabric;
    a padding layer positioned in-between the inner and outer layers; and
    the outer, padding, and inner layers being joined together.

11. The textured bra insert of claim 10, wherein the outer, padding, and inner layers are joined together either with a seam or seamlessly.

12. The textured bra insert of claim 11, wherein the outer, padding, and inner layers are joined together seamlessly by ultra sonic welding, laser, heat, or hot air.

13. The textured bra insert of claim 10, wherein the hexagon shapes are 0.125 inches in diameter with 0.1875 inches in height, and evenly spaced apart at 0.125 inches from each other.

14. The textured bra insert of claim 10, wherein the textured fabric is made from a spandex blend, the blend having at least 20% spandex.

15. The textured bra insert of claim 10, wherein the moisture wicking fabric is made from a blend of polyester and spandex, or nylon and spandex.

16. The textured bra insert of claim 10, wherein the shape of the insert is one of a full, demi, mini, push-up, Bandeau styled, oval, round, triangle, or prosthetic breast.

17. The textured bra insert of claim 10, wherein the raised pattern of discontinuous geometric shaped silicone material covers no more than 20 millimeters per square inch of the stretchable fabric.

18. A textured bra insert, comprising:
    a three dimensional (3-D) spacer fabric molded in the form of an insert, having an outside surface and an inside surface, the outside surface being stretchable fabric; and
    the outside surface having been deposited with a raised pattern of discontinuous geometric shaped material.

19. The textured bra insert of claim 18, the geometric shape being a hexagon shape sized between 0.063 inches and 0.5 inches in diameter and is between 0.063 inches and 0.375 inches in height, and is spaced apart between 0.125 inches to 0.375 inches from each other.

20. The textured bra insert of claim 18, wherein the shape of the insert is one of a full, demi, mini, push-up, Bandeau styled, oval, round, triangle, or prosthetic breast.

\* \* \* \* \*